(12) United States Patent
Puurunen et al.

(10) Patent No.: US 8,585,411 B2
(45) Date of Patent: *Nov. 19, 2013

(54) INTELLIGENT TOOTHBRUSH MONITORING DEVICE

(71) Applicant: Brushgate Oy, Helsinki (FI)

(72) Inventors: Juha-Pekka Puurunen, Lapinlahti (FI); Ari Visa, Espoo (FI); Jussi Collin, Viiala (FI); Jouni Kantola, Eura (FI); Ivan Avdouevski, Tampere (FI); Ulf Meriheina, Soderkulla (FI); Teijo Viljanen, Espoo (FI)

(73) Assignee: Brushgate Oy, Helsinki (FI)

( * ) Notice: Subject to any disclaimer, the term of this patent is extended or adjusted under 35 U.S.C. 154(b) by 0 days.

This patent is subject to a terminal disclaimer.

(21) Appl. No.: 13/663,722

(22) Filed: Oct. 30, 2012

(65) Prior Publication Data

US 2013/0074616 A1    Mar. 28, 2013

Related U.S. Application Data

(62) Division of application No. 12/131,795, filed on Jun. 2, 2008, now Pat. No. 8,337,213.

(30) Foreign Application Priority Data

May 23, 2008    (FI) .................................. 20085488

(51) Int. Cl.
G09B 23/28    (2006.01)

(52) U.S. Cl.
USPC ........... 434/263; 434/262; 446/268; 15/167.1

(58) Field of Classification Search
USPC .................................... 434/262, 263; 446/268
See application file for complete search history.

(56) References Cited

U.S. PATENT DOCUMENTS

2006/0040246 A1*    2/2006    Ding et al. .................... 434/263
2009/0092955 A1*    4/2009    Hwang ......................... 434/263

* cited by examiner

Primary Examiner — Xuan Thai
Assistant Examiner — Banafsheh Hadizonooz
(74) Attorney, Agent, or Firm — Christopher Paradies; Paradies Law P.A.

(57) ABSTRACT

A toothbrushing monitoring device for a user includes a sensor coupled with the toothbrush for measuring toothbrushing patterns, a recording device coupled with the sensor, and a comparator. The recording device records data relating to the user's preferred toothbrushing patterns in a first mode, which is used to establish toothbrushing pattern reference data. The comparator compares toothbrushing patterns measured by the sensor and the toothbrushing pattern reference data, which may be output to an output device. In one example, the sensor consists of only an accelerometer.

16 Claims, 6 Drawing Sheets

INTELLIGENT TOOTHBRUSH MONITORING DEVICE

REFERENCE TO RELATED APPLICATIONS

This application is a divisional application of U.S. patent application Ser. No. 12/131,795 filed Jun. 2, 2008 (now pending), which claims the benefit of the filing date of Finnish Patent Application, FI-20085488, filed on May 23, 2008.

FIELD OF THE INVENTION

The field relates to a device for monitoring the use of a toothbrush in order to give the user feedback about brushing.

BACKGROUND OF THE INVENTION

WO 2006/137648 discloses a device for analyzing patterns comprising a geomagnetic sensor, an acceleration sensor, and an angular velocity sensor for analyzing the patterns used during brushing. The device compares the amount of a user's effective motion with a target, and informs the user when the target has been reached.

One drawback with this known device is the costs involved in producing such a device. The price of the components needed to produce the device and also the space needed by the components are significant, making the device impractical.

Another drawback is that the device does not account for individual factors involved in brushing. Each individual person brushes their teeth using their own individual brushing patterns, head orientation toothbrush positions. The device of WO 2006/137648 requires everyone to conform to its standard and habits.

WO 2006/137648's corresponding application WO 2006/137661 discloses a system that includes a lifetime periodic toothbrushing method database server that toothbrushing method related data, an analysis part that analyzes tooth brushing patterns, and a personal feedback data generation part, which generates feedback data in response to the analyzed toothbrush pattern. This system, only determines whether dental treatment is needed or not based on a comparison with an ideal toothbrushing pattern.

U.S. Pat. No. 6,536,068, discloses use of either a multi-axis accelerometer with a strain gage or a three-dimensional force sensor for monitoring brushing.

SUMMARY OF THE INVENTION

A monitoring device provides a more cost-effective and space saving solution for monitoring toothbrushing. In addition, the system captures and retains individual brushing patterns in a first mode that may be used for comparisons in a second mode of operation.

A monitoring device includes a sensor coupling with the toothbrush and measuring toothbrushing patterns, a recording device coupled with the sensor, the recording device recording data relating to the user's preferred toothbrushing patterns in a first mode, and a comparator for comparing the toothbrushing pattern reference data to toothbrushing patterns measured by the sensor in a second mode during daily use, for example. The first mode may be used to capture and retain toothbrushing pattern reference data. In another example, the toothbrush monitoring device further comprises an output device coupled to the comparator for providing feedback to the user. For example, the output device may be electronically or wirelessly coupled to the comparator or to an intermediate device. The output device may comprise an indicator, an interface for coupling to a remote device, or a combination of both an indicator and an interface. The output device may provide a sound, image, color, smell, tactile feedback, or a combination of these to give feedback to the user based on a comparison between the data recorded by the recording device and the toothbrushing patterns measured by the sensor.

In one example, the toothbrush monitoring device includes a sensor apparatus. For example, the sensor apparatus consisting solely of an accelerometer, which may be integrated in a device or a toothbrush to measure toothbrushing patterns. For example, toothbrushing patterns, may include data indicating inclination of a toothbrush during use. Thus, toothbrushing patterns generate toothbrushing patterns data using a toothbrushing sensor, which may consist of an accelerometer. In one example, additional cost-increasing and space-consuming sensor components are not needed to track the movement or position of a toothbrush. In one example, a device includes a recording device that allows the user to set the device into a recording or teaching mode, such that the data produced by the sensor is stored as a user's own, preferred toothbrushing patterns for subsequent use. In one example, by using the recording device, the user may at any desired point of time, store user's own toothbrushing patterns into the recording device.

A method of monitoring a user's toothbrushing using a toothbrush monitoring device, comprises: recording data relating to the user's toothbrushing patterns in a first mode of the toothbrush monitoring device, measuring toothbrushing patterns using the sensor of the toothbrushing monitoring device in the second mode of the toothbrush monitoring system, and comparing the toothbrushing patterns measured in the step of measuring to the data recorded in the step of recording.

One advantage of a device using only an accelerometer device is that the costs to produce the device are reduced. Another advantage is that use of an accelerometer without other displacement orientation or position sensors conserves space.

Yet another advantage of a device is the ability to having a mode for capturing and retaining take in account a user's preferred toothbrushing patterns and compares the user's preferred toothbrushing patterns with toothbrushing patterns measured by the sensor during an operating mode.

DETAILED DESCRIPTION

The examples described and the drawings rendered are illustrative and are not to be read as limiting the scope of the invention as it is defined by the appended claims.

Figure 1:
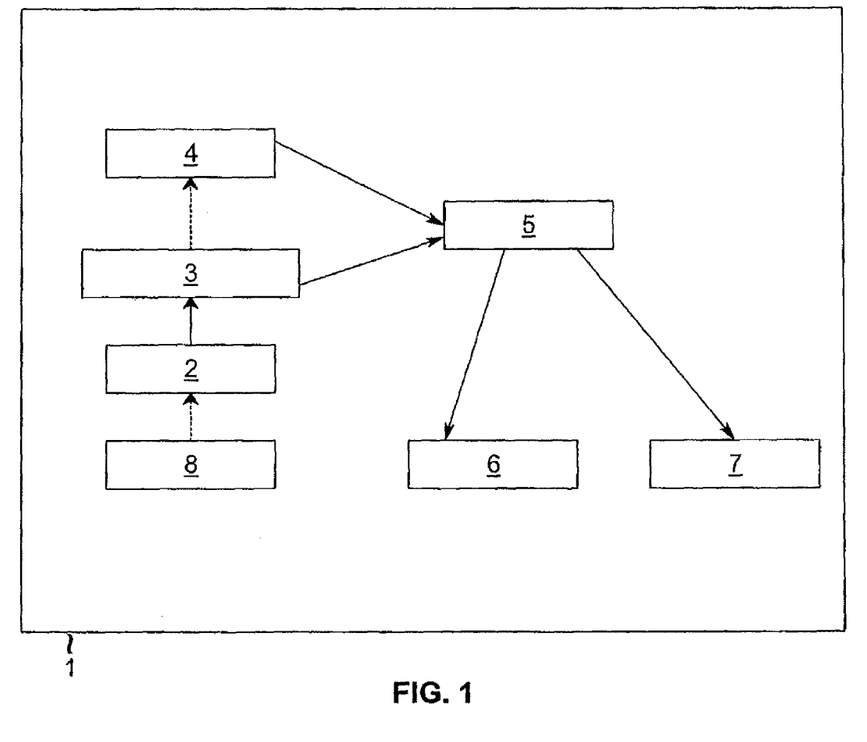
FIG. 1 is a block diagram illustrating an example of a monitoring system.

FIG. 1 is a block diagram illustrating an example of a monitoring device 1. The monitoring device may be integrated into a toothbrush or alternatively consist of a separate component that is attached to a toothbrush. By being a separate component, the monitoring device may be detached from the first toothbrush and may be attached to another toothbrush.

In this example, the monitoring device comprises a controller 2 controlling the operation of the monitoring device. The controller 2 and the comparator 5 may be carried out with circuitry or use a combination of a computer program and circuitry. In the latter case, a processor running on a computer may carry out the tasks of the controller 2 and/or the comparator 5 under control of software. The computer may be a stand alone processor, such as incorporated into a base device or may be a general purpose computer.

In one example, a sensor is coupled to the device for measuring toothbrushing patterns. In one example of a sensor, a three-axis accelerometer 3 is utilized to detect the inclination of the toothbrush during use, such as the angles at which the toothbrush and the monitoring device attached to the toothbrush are held during use. The accelerometer may be a SCA 3000 available from VTI Technologies Oy, P.O. Box 27, FI-01621 Vantaa, Finland, for example.

The output of a three-axis accelerometer may be expressed as:

$$\bar{m}_{SF}^{B} = \frac{d}{dt}\bar{v}^{B} - \bar{g}^{B} + \bar{\varepsilon} \quad (1),$$

where the result vector (3 components) corresponds to the change in the velocity of an object, reduced by the gravitation vector. In addition, an error term may be included. The upper index B (Body frame) refers to a coordinate system attached to the accelerometer (in this case, a monitoring device). Measurements may be done in this coordinate system.

The result does not, therefore, consist of acceleration only, and in literature, the term "Specific Force" is utilized. Specific force acceleration is defined as the acceleration relative to non-rotating inertial space produced by applied non-gravitational forces measured by accelerometers.

From equation (1), an accelerometer may be used to measure both inclination (when the change of velocity is known) and acceleration (when gravitational acceleration in body frame is known). In the measurements carried out with the monitoring device 1, acceleration is assumed to be noise disturbing the inclination or angle measurements.

During toothbrushing, an accelerometer 3 may measure toothbrushing patterns, which may be recorded or supplied data to the comparator 5. In an example of toothbrushing patterns data, the toothbrushing patterns data of FIGS. 11a-11d indicates the inclination or angles, at which the monitoring device 1 and toothbrush are held during use. The comparator 5 may receive toothbrushing pattern reference data from the memory 4, also. A memory 4 may be a recording device that is coupled with the accelerometer, for retaining pattern reference data. For example, toothbrushing pattern reference data may be compared with the data produced during normal, daily use of a toothbrush once the use of the toothbrush has finished. In one example of toothbrushing pattern reference data, the toothbrushing pattern reference data may also indicate the time used (seconds, for instance) and the brush order (transfer from one position to another). The comparison of toothbrushing pattern data during use with the toothbrushing pattern reference data is used to give feedback to the user with an indicator 6, which is an example of an output device. An output device may be coupled to the comparator for providing feedback to the user. In one example, an indicator may consist of a single LED (Light Emitting Diode) which informs the user, by flashing a predetermined way, whether or not the result of the toothbrushing is accepted or not accepted. Alternatively, the indicator 6 may comprises display, such as, an LCD (Liquid Crystal Display) a voice message, or of several LEDs which are used to indicate what parts of the teeth were not brushed thoroughly enough. The monitoring device may be configured to automatically inform the user about the results of the brushing analysis, using toothbrushing with the LED, plurality of LED's or display by indicating the result for a predetermined time period after the brushing has completed, as determined by timeout, return to a base, or a switch, for example.

Instead of a visual indicator, an indicator which produces sound, such as a buzzer producing a predetermined beep or a speech generator producing instructions after toothbrushing in a case where the result is not acceptable, may be used to indicate either success or unacceptable brushing. In this way, the user may be provided immediate feedback regarding brushing.

In the system of FIG. 1, a monitoring device 1 also includes an interface 7 for forwarding the result of the comparison to a remote device. An interface 7 may include an output device. Such an interface may not be used in all embodiments, and sufficient feedback may be provided to the user via the indicator 6. A monitoring device may include an indicator, an interface, or a combination of both an indicator and an interface.

In the case of a wired connection to a remote output device, the interface may include electrical contacts, which are used by the monitoring device for communication with the remote device. Alternatively, in the case of a wireless interface 7, the interface 7 may include a radio transmitter for transmitting the measurement result via a radio path to the remote device.

The monitoring device 1 may also use a switch 8 for setting the monitoring device into a first mode, which may be used for collecting the users own preferred brushing pattern data. The first mode may be continuous, meaning that data is stored for reference continuously, including the toothbrushing patterns measured by the sensor, or may be used to store data selectively. Selective data may be used under dental hygienist, dentist or parental supervision to insure adequate brushing, for example. After actuation of a switch 8, the accelerometer 3 is configured to measure and forward toothbrushing pattern data (for example, the data relating to an inclination of a toothbrush) to memory 4, where it may be processed and stored for subsequent use during the use of the toothbrush.

The accelerometer measures toothbrushing patterns for comparison with reference data when the monitoring device is in a second mode. The first mode allows the user to store individual toothbrushing pattern reference data into the memory 4. For example, after pressing the switch 8, the user uses the toothbrush to brush his or her teeth as thoroughly as desired. Second actuation of the switch 8 may end the first mode. The result is that toothbrushing pattern reference data indicating angles at which this particular user holds the toothbrush during use is stored in the memory as a preferred toothbrushing pattern reference data. In addition, the reference data may also indicate the time used and the brush order (transfer from one position to another). This individual toothbrushing pattern reference data may be used for analyzing how thoroughly this particular user will brush his or her teeth in the future during daily use. The first mode therefore allows the user to take into account individual behaviour (the toothbrush or the user's head is held at individual angles, for instance) while brushing the teeth.

When the toothbrushing monitoring device is used in daily use, a comparison may be made with the reference data retained by the system. Additional reference data may be recorded to replace or aggregate with the first reference data. Such toothbrushing patterns may be stored either individually or collectively as toothbrushing pattern reference data in a recording device. For example, a user, in one particular brushing session, may store the produced toothbrushing patterns in the recording device as reference data. Alternatively, the user may add such reference data to a cumulative toothbrushing pattern reference data.

Individual toothbrushing pattern reference data may be stored for a plurality of persons within the memory coupled to the monitoring device. In one example, an identifier of the person who used the toothbrush during the teaching mode is stored in the memory together with the toothbrushing pattern reference data. In one example, this identifier associated with the individuals brush head on a device having one brush head for each individual user. This presents an advantage in a case where several persons use the same toothbrush or handle (with their own personal attachable brush parts, such as a brush head). In that case, the monitoring device may be able to automatically identify the person using the toothbrush by selecting the toothbrushing pattern reference data that best matches the data produced during the use of the brush. Alternatively, the toothbrush may include an interface, which allows the user the ability to enter his or her identifier in order for the monitoring device to be able to select the correct toothbrushing pattern reference data from the memory.

Figure 2:
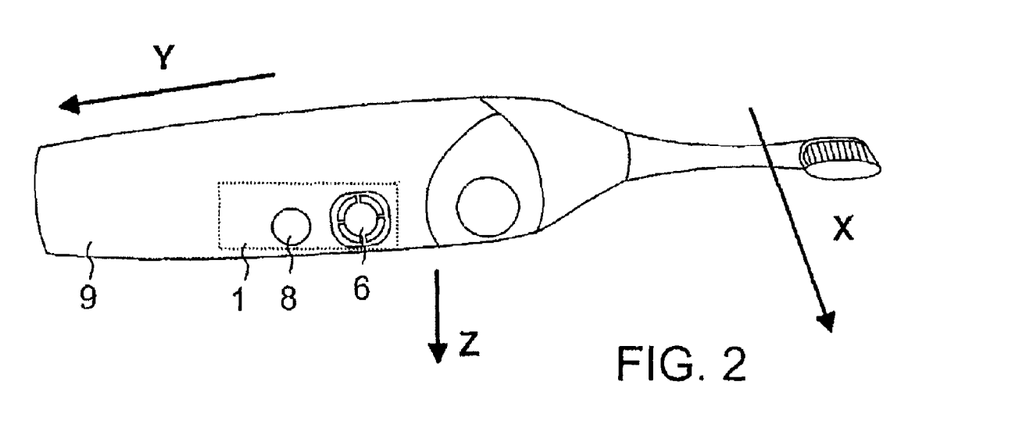
FIG. 2 illustrates an example of an electric toothbrush, such as a toothbrush using a monitoring system of FIG. 1.

FIG. 2 illustrates an example of electrical toothbrush 9 with a monitoring device of FIG. 1. In the case of an electrical toothbrush, the energy needed to operate the monitoring device may be taken from the same battery, which is used to energize the electrical motor of the toothbrush. The monitoring device 1 may be integrated into the electrical toothbrush 9, as illustrated, or alternatively attached as an extension to the body (the left end in FIG. 2) of the toothbrush 9.

For the purpose of illustrating the coordinate systems used for producing the diagrams in FIGS. 6 to 9, the directions of the X-axis, Y-axis and Z-axis are indicated in FIG. 2. For clarifying purposes, the direction of the X-axis is generally the same as the direction of the bristles in the brush, the direction of the Y-axis is generally the same as the direction of the center line of the tubular body of the toothbrush, and the Z-axis is generally directed sideways from the body of the toothbrush, thus forming a 90° angle with the X- and Y-axis. It should, however, be observed that the exact directions of the axes are not important for the monitoring device as such, but only in order to be able to understand the angles illustrated in the exemplary diagrams of FIGS. 6 to 9.

Figure 3:
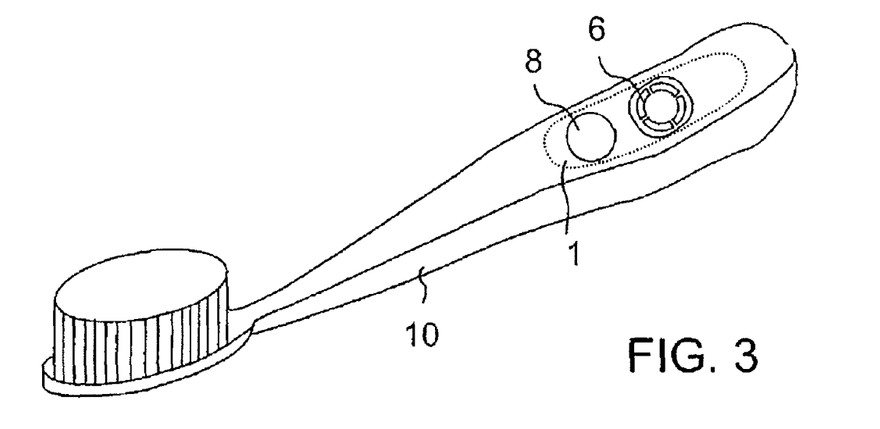
FIG. 3 illustrates an example of toothbrush, such as a toothbrush using a monitoring system of FIG. 1.

FIG. 3 illustrates an example of a non-electric toothbrush with the monitoring device of FIG. 1. Also in this embodiment, the monitoring device has been integrated into the toothbrush 10. Alternatively, a separate monitoring device may be attached to the toothbrush 10 (as an extension to the handle, for example), and detached for use in another toothbrush once the old toothbrush is replaced with a new one.

Figure 4:
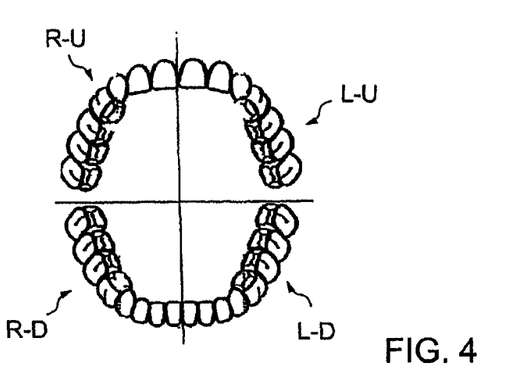
FIGS. 4 and 5 illustrate examples indicating four regions for brushing and teeth (FIG. 4) or only regions (FIG. 5).
Figure 5:
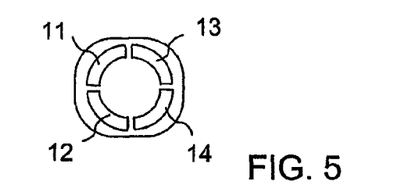

FIGS. 4 and 5 illustrate one way of indicating the result of toothbrushing to a user. Four different regions of teeth may be identified, as illustrated in FIG. 4. Left-up L-U, left-down L-D, right-up R-U and right-down R-D regions may be identified. In many cases, sufficient feedback may be given to the user by indicating that one (or more) of these four regions has not been brushed thoroughly enough. This may be accomplished using an indicator such as illustrated in FIG. 5, an example of an output device. This indicator, which may use four LEDs or an LCD display, for instance, includes one sector 11 to 14 for each region shown in FIG. 4. If sector 11 is illuminated in red on the indicator of FIG. 5 after brushing, the user understands that region R-U of FIG. 4 requires more thorough brushing, for instance. Similarly, if another sector 13 is illuminated in red on the indicator of FIG. 5 after brushing, the user understands that region L-U of FIG. 4 requires more thorough brushing, for instance. Acceptable brushing may be indicated by illuminating in another color, such as green, for example. Alternatively, other colors and ways of illuminating the indicator may be utilized in order to provide the user with feedback, such as flashing versus solid, lit versus unlit, and the like.

Figure 6:
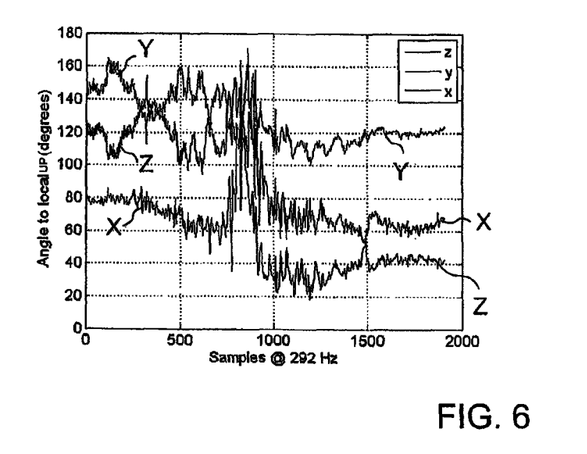
FIGS. 6 and 7 illustrate measurements using an accelerometer during toothbrushing with an electric toothbrush, such as shown in FIG. 2.

FIGS. 6 and 7 illustrate measurements carried out during toothbrushing with the electrical toothbrush 9 of FIG. 2. FIG. 6 illustrates toothbrushing patterns data, data produced by the accelerometer 3 while the electrical toothbrush 9 is used to brush the inside of the teeth of the upper jaw, in other words, data from the inside of regions L-U and R-U in FIG. 4, moving the brush from left to right (as seen by the user) are provided. A substantial change in the Z-angle may be seen around sample 800, where the brush is turned by the user in the front part of the teeth while moving from region L-U to R-U.

Figure 7:
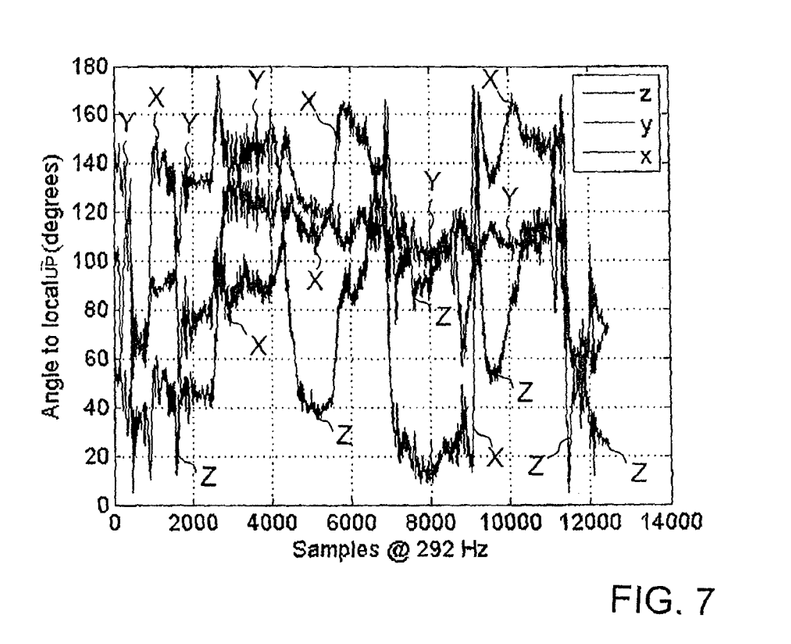
Figure 8:
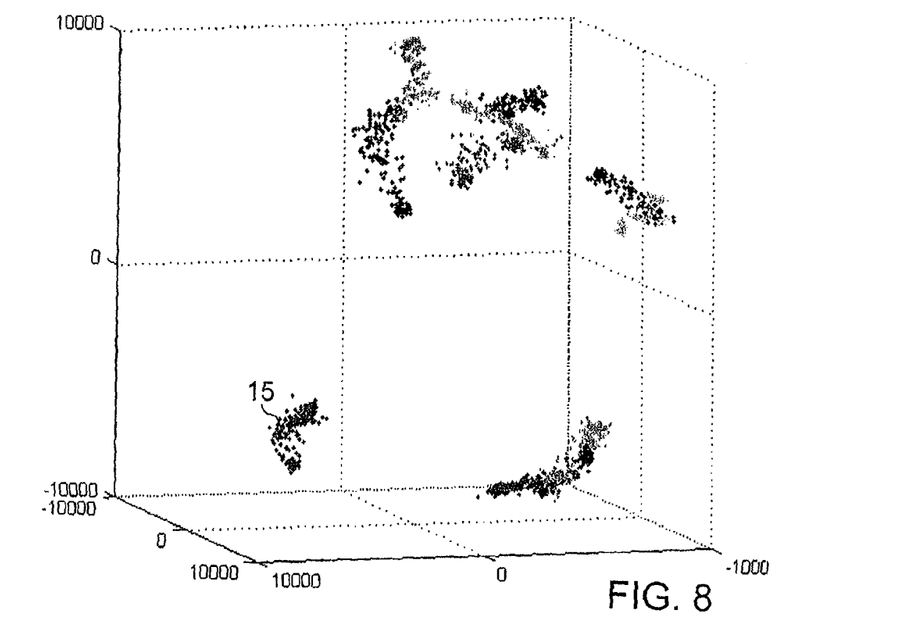
FIG. 8 illustrates toothbrushing pattern reference data stored by one example of a toothbrush monitoring device.

FIG. 7 illustrates similar toothbrushing patterns data with the difference that the electrical toothbrush 9 is used to brush all teeth. The brushing order is from the upper outer surfaces from left to right, then the right lower outer surface towards left, lower biting surfaces from left to right, upper biting surfaces from right to left, and finally, upper inner surfaces from left to right and lower inner surfaces from right to left. On the basis of the diagram of FIG. 7, it can be seen that the angle combination used while brushing different parts of the teeth is different. On the basis of the angle combinations (values of X, Y and Z angles), the device may identify which part of the mouth has been brushed. This is illustrated more clearly in FIG. 8. FIG. 8 illustrates toothbrushing pattern reference data stored in the memory of the monitoring device. In FIG. 8, the output from the accelerometer while brushing different parts of the teeth is shown three-dimensionally. In FIG. 8, samples, which are located in proximity to a plurality of other samples, are illustrated. It can be seen that the data includes several clusters of samples for different angle combinations. For example, cluster 15 consists of samples obtained while brushing the right upper inner surface of the teeth, the toothbrush being, during the moments when these samples are taken, kept relatively steady in a particular inclination (angle combination). If a person intends to brush his or her teeth as thoroughly as when the toothbrushing pattern reference data illustrated by the clusters in FIG. 8 was obtained, then the accelerometer should produce data from which a similar cluster pattern can be identified. If one of the clusters is missing, for instance cluster 15, then a specific combination of angles (XYZ) which is needed in order to obtain samples for this cluster may be determined. Based on this angle combination (with a certain accuracy or within a range for each angle), one is able to determine the part of the teeth, in this case, the right upper inner surface of the teeth, that has not been brushed thoroughly enough. This information may be provided to the user with the indicator of the monitoring device previously described or any other output device.

Figure 9:
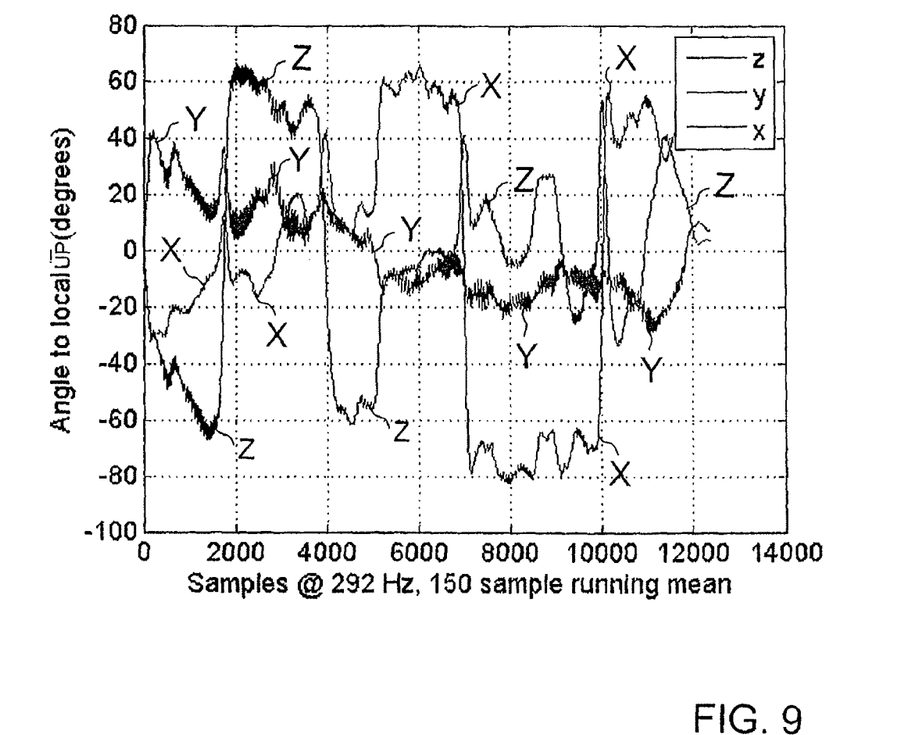
FIG. 9 illustrates measurements carried out during toothbrushing with a toothbrush, such as the toothbrush of FIG. 3.

FIG. 9 illustrates measurements carried out during toothbrushing with the toothbrush 10 of FIG. 3. The toothbrush 10 in this figure is not electrical. As the toothbrush 10 is not electrical, the user must therefore continuously move the brush back and forth and a pattern with a frequency of about 4-5 Hz is included in the signal from the accelerometer. In FIG. 9, this signal has been eliminated by low pass filtering, for example. When using a non-electrical toothbrush, a monitoring device 1 may be utilized to determine the angles used during brushing. A solution similar to the one for the electrical toothbrush may be used to analyze how thoroughly the user has brushed his or her teeth, and to indicate regions, which need additional brushing, for example. With the non-electrical toothbrush 10, additional information is, however, available. This additional information may be seen in FIG. 9 as a peak for each time the user has moved the brush to brush a tooth or a plurality of teeth. The device may calculate the number of such movements in order to determine how many times the user has moved the brush during brushing. In order to obtain a brush result which is as thorough as the one for the toothbrushing pattern reference data (a first mode), the number of movements may at least not be substantially smaller than the number of movements indicated by the toothbrushing pattern reference data. Thus, a threshold range may be provided for acceptable brushing patterns based on the user's preferred brushing pattern reference data.

The additional information indicating the number of times the user has moved the brush to brush a plurality of different teeth may also be utilized for determining when the brush needs to be replaced. This may be achieved by arranging the monitoring device to maintain a counter indicating the number of such movements performed with the specific brush since the brush was taken into use for the first time. If the counter reaches a predetermined limit value, the monitoring device may indicate to the user with an indicator that it is time to replace the brush, for example.

Figure 10:
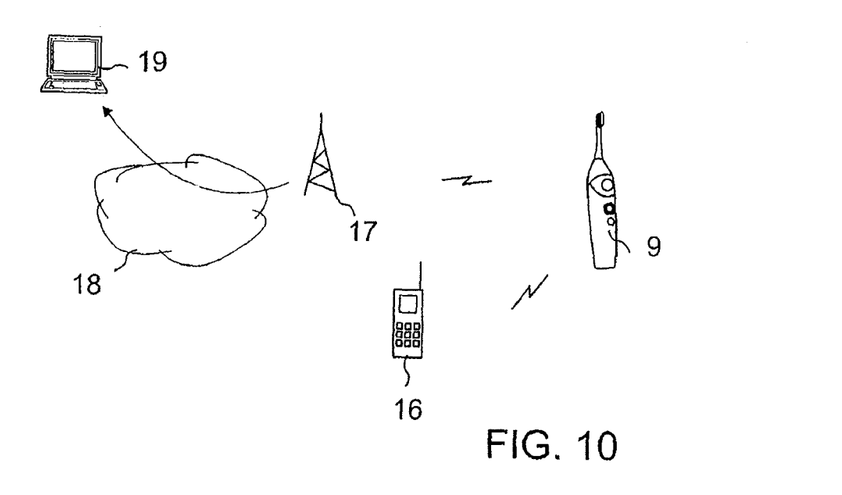
FIG. 10 illustrates data transfer from an example of the monitoring device incorporated into a toothbrush to external equipment, such as a cell phone or a computer.

FIG. 10 illustrates data transfer from a monitoring device to external equipment. In FIG. 10, the monitoring device used for the electrical toothbrush 9 of FIG. 2 includes an interface with a radio transmitter for forwarding the result of the comparison to a remote device. In one example, the monitoring device may include an additional switch and user interface. The user interface may be used by the user in order to trigger transmission of the comparison of the toothbrushing pattern reference data with the toothbrushing patterns data to the remote device. Alternatively, the transmission may occur automatically each time the toothbrush has been used, or may be triggered by placing the toothbrush in a cradle or base.

All parts of the monitoring device may be encapsulated with each other and/or may be integrated into or attached to the body of the electrical toothbrush 9. Alternatively, a radio transmitter may be arranged separately from the other parts, for instance, in a battery charger, cradle or base of the electrical toothbrush 9. In that example, the interface 7 may include contact terminals in the toothbrush 9, which are connected to the corresponding terminals in the battery charger for forwarding the result of the comparison via a wired connection to the transmitter in the battery charger or may be connected by induction or short range wireless communications. The radio transmitter in the battery charger then transmits this comparison result further via the wireless radio connection to the remote device.

In FIG. 10, the remote device may be a mobile phone 16, PDA or computer 19, which receives the information directly from the monitoring device via a short range radio connection, as one example of a transmitter, such as a Bluetooth or a Wibree connection. In one example, the user of the remote device may receive information about how thoroughly the toothbrush 9 has been used or the need to provide a replacement brush.

FIG. 10 also illustrates an alternate example of a transmitter, using an intermediate receiver 17 and a network 18, such as a cellular radio system. Also in this example, the radio transmitter may be located in connection with the electrical toothbrush 9 or alternatively in connection, with a charger, cradle or base station of the electrical toothbrush 9. In such an example, the comparison result may be transmitted via an intermediate receiver 17 and the network 18 to a remote device 19, 16 located further away than the range of a short range radio system, for example. The remove device 19, 16 may be any device suitable for receiving the signals from the network 18 and providing feedback on an output device.

The transmission of information via a cellular radio system to the remote device may allow an advertiser provide an advertisement. For example, an advertisement may be added to the comparison result using network elements in the cellular radio system. The user may receive an advertisement with the comparison result. An advantage with such a solution is that the advertiser may provide revenue offsetting all or a portion of the cost for the transmission of the comparison result from the toothbrush 9 to the remote device 19, 16.

Though the monitoring device has been explained by referring specifically to a three axis accelerometer, a three axis accelerometer another sensor or sensors may be used. For example, even a two axis accelerometer allows a device to obtain a substantial portion of the information about the inclination of the toothbrush during use. In addition, an n-axis accelerometer allows a device to determine an angular acceleration in addition to an inclination of the toothbrush. Other sensors may be used to capture information yielding results similar to an accelerometer.

Figure 11A:
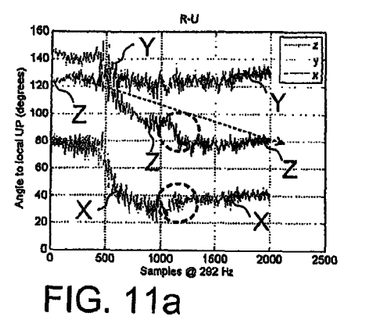
FIGS. 11a to 11d illustrate an example of determining which part of the teeth is being brushed using only an accelerometer.
Figure 11B:
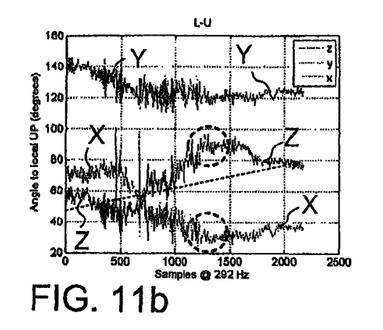
Figure 11C:
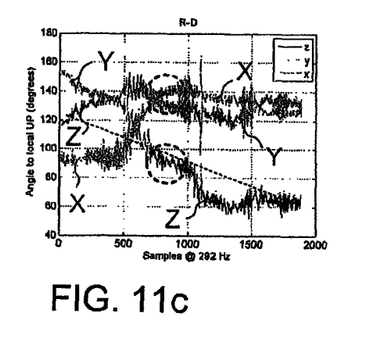

FIGS. 11a to 11c illustrate a solution for determining which portion of the teeth is being brushed. This solution may be used in order to indicate to a user the result of toothbrushing as explained in connection with FIGS. 4 and 5, for example. In this example, the user may be instructed to brush each of the four illustrated regions R-U, L-U, R-D and L-D completely before moving to the next region. In addition, each one of the four regions may be brushed in a specific order: outer surface, mastication surface and inner surface as preferred by the user. So long as each region is brushed in this order, it may not matter in which order the user brushes the four different regions, as the monitoring device is able to identify the brushed region automatically and to indicate the result of the brushing by using the correct sector 11-14 on the indicator, during brushing or thereafter.

Figure 11D:
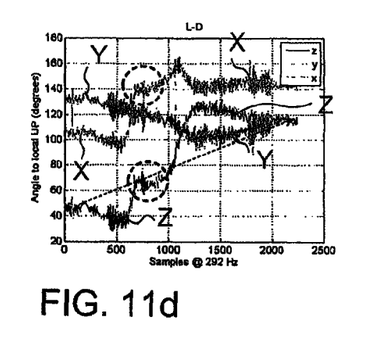

FIG. 11a illustrates brushing of region R-U in the following brushing order: an outer surface, a mastication surface and an inner surface. Correspondingly, FIGS. 11b to 11d illustrate brushing of regions L-U, R-D and L-D by using the same brushing order for each region. When brushing in this way, the region being brushed can be identified based on two factors:

1) when the Z axis is horizontal, in other words, when the angle value indicated in the measurement results of FIGS. 11a to 11d for Z is 90°, the value of X is analyzed. If X is more than 90°, this means that one of the lower regions (R-D, L-D)

is being brushed. However, if X is less than 90°, then one of the upper regions (R-U, L-U) is being brushed.

2) if the value of Z is (generally) decreasing during brushing of one region, this means that one of the right hand regions (R-D, R-U) is being brushed. However, if the value of Z is (generally) increasing during brushing of the region, this means that one of the left hand regions (L-D, L-U) is being brushed.

Therefore, in this example, the monitoring device 1 is configured to analyze the above mentioned angles during the first mode, capturing reference data, and also during subsequent use of the brush. In this way, the monitoring device is capable of identifying the region, which is currently being brushed. After brushing, the toothbrushing pattern reference data and the toothbrushing patterns data produced during use of the toothbrush, for each one of the regions, is compared to each other. In one example, if a region for which the number of samples or time spent by keeping the brush in this region as indicated by the toothbrushing pattern reference data is identified and does not correspond to the number of samples or time spent as indicated by the data produced during subsequent use, then the sector 11 to 14 for this region on the indicator may be used to inform the user of improper brushing technique in one or more of these regions. In another example, the user may brush each one of the regions of FIG. 4 in any desired way. Also in this example, a region may be completely brushed before proceeding to the next region. However, the four regions may be brushed in any order. In this example, however, it may be more difficult for the monitoring device to identify the particular region, which is being brushed. The monitoring device may simply include an indicator with sectors numbered from one to four. Once the user has brushed a first region, the result is indicated by using the first sector of the indicator. Once the user has brushed a second region, the result is indicated by using the second sector. Once the user has brushed a third region, the result is indicated by using the third sector, and so on. Consequently, in this example, the monitoring device does not identify to the user a particular region for which improper or proper brushing has been identified. Instead, the monitoring device identifies sector 3 to indicate that the success or failure of properly brushing the third brushed region. In this example, the user may remember which region was the third brushed region and/or the sequence of brushing preferred by the user.

Figure 12:
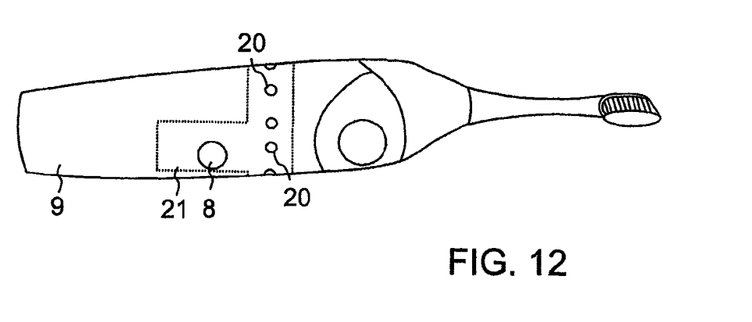
FIG. 12 illustrates another example of a toothbrush with an output device integrated into the handle.

FIG. 12 illustrates another example of a toothbrush with a monitoring device. The device of FIG. 12 is very similar as the one described in connection with FIG. 2. Therefore, the device of FIG. 12 is an electric toothbrush 9; however, it has a plurality of indicator lights 20.

In this example, the indicator includes a plurality of LED's, for instance, arranged as a ring around the body of the electrical toothbrush 9. One alternative includes eight LED's 20 a ring around the toothbrush 9.

During daily use, the monitoring device 21, compares data to reference data obtained for a particular angle position. As soon as it is determined that the produced toothbrushing pattern data and the toothbrushing pattern reference data match, perhaps within a threshold, one of the LED's in the indicator 20 may be illuminated and/or a sound, vibration or other indicator may alert the user to move to the next region. In this example, the monitoring device may illuminate the LED which is directed towards a predetermined direction, such as an upwards direction, at that particular moment, or may provide a relative alert.

Once the user has completed the toothbrushing, the monitoring device may have illuminated (one-by-one) each one of the LED's. Thus, if the user observes that one of the LED's has not been illuminated, this means that the toothbrush has not been sufficiently used during brushing in a position corresponding to the LED not illuminated, for example. The user may return the brush to such a position in order to properly complete the brushing of one or more regions not illuminated or otherwise indicated as improperly brushed, such as a difference color or flashing indicator.

Alternative combinations and variations of the examples provided will become apparent based on this disclosure. It is not possible to provide specific examples for all of the many possible combinations and variations of the embodiments described, but such combinations and variations may be claims that eventually issue.

What is claimed is:

1. A toothbrush monitoring device for a user using a toothbrush, comprising:
   a processor;
   an output device for providing feedback to the user;
   a sensor coupling with the toothbrush for measuring toothbrush patterns, the sensor consisting of an accelerometer such that the accelerometer produces data indicating inclination of the toothbrush;
   a recording device coupled with the processor and the sensor, the recording device being arranged such that reference data relating to a preferred toothbrush pattern is captured by the sensor and stored in the recording device for a plurality of teeth regions, when in a first mode, during use of the toothbrush by the user in the first mode for recording the reference data; and
   a comparator coupled with the output device, the processor, the sensor and the recording device such that the comparator compares in the recording device for each of the plurality of teeth regions the reference data to data measured by the sensor, during use of the toothbrush in a second mode, and the comparator indicates with the output device one or more of the plurality of the teeth regions not brushed according to the reference data relating to the preferred toothbrush pattern.

2. The toothbrush monitoring device of claim 1, wherein the sensor is coupled to a switch, and the switch is switchable by the user to activate the first mode.

3. The toothbrush monitoring device of claim 1, wherein the accelerometer comprises a three-axis accelerometer.

4. The toothbrushing monitoring device of claim 1, wherein the comparator is capable of determining information relating to the preferred brushing of at least a portion of the user's teeth from a comparison of the reference data recorded by the recording device in the first mode and the data measured by the sensor in the second mode using the comparator, without any other sensors providing any additional information to the comparator.

5. The toothbrush monitoring device of claim 1, wherein the output device comprises an indicator, an interface for coupling to a remote device, or a combination of both an indicator and an interface.

6. The toothbrush monitoring device of claim 1, wherein the output device comprises an indicator.

7. The toothbrush monitoring device of claim 6, wherein the indicator comprises at Least one light-emitting diode.

8. The toothbrush monitoring device of claim 7, wherein the indicator comprises a plurality of light-emitting diodes arranged in a ring around a body of the toothbrush or the toothbrush monitoring device.

9. The toothbrush monitoring device of claim 8, wherein each of the plurality of light-emitting diodes corresponds to a toothbrush position or toothbrush angle used in toothbrushing.

10. The toothbrush monitoring device of claim 1, wherein the output device includes the interface for coupling to the remote device.

11. The toothbrush monitoring device of claim 10, wherein the interface includes a transmitter.

12. The toothbrush monitoring device of claim 11, wherein the transmitter includes a short range radio transmitter.

13. The toothbrush monitoring device of claim 11, wherein the transmitter includes a cellular system transmitter.

14. The toothbrush monitoring device of claim 1, further comprising:
- a toothbrush handle and a toothbrush head having bristles extending from the head, wherein the sensor, the recording device and the comparator are integrated into the toothbrush handle.

15. The toothbrush monitoring device of claim 1, wherein
- the output device comprises an indicator having four sectors, a first of the four sectors indicating a Left-Up region of the teeth, a second of the four sectors indicating a Left-Down region of the teeth, a third of the four sectors indicating a Right-Up region of the teeth and a fourth of the four sectors indicating a Right-Down region of the teeth, and
- the indicator of the output device is arranged to indicate whether or not brushing of the corresponding one of the four sectors was according to the reference data, relating to the preferred toothbrush pattern.

16. The toothbrush monitoring device of claim 1, wherein the indicator of the output device provides sound, image, color, smell, tactile feedback or a combination of these.

* * * * *